(12) United States Patent
Popowski et al.

(10) Patent No.: US 8,246,528 B2
(45) Date of Patent: Aug. 21, 2012

(54) IMPLANT FOR TREATING THE INTERNAL WALLS OF A RESECTION CAVITY

(75) Inventors: Youri Popowski, Geneva (CH); Erwin Berger, Settfurt (CH)

(73) Assignee: Acrostak AG, Winterthur (CH)

(*) Notice: Subject to any disclaimer, the term of this patent is extended or adjusted under 35 U.S.C. 154(b) by 872 days.

(21) Appl. No.: 12/087,454

(22) PCT Filed: Jan. 8, 2007

(86) PCT No.: PCT/EP2007/000077
§ 371 (c)(1),
(2), (4) Date: Feb. 2, 2009

(87) PCT Pub. No.: WO2007/080075
PCT Pub. Date: Jul. 19, 2007

(65) Prior Publication Data
US 2009/0306453 A1 Dec. 10, 2009

(30) Foreign Application Priority Data
Jan. 10, 2006 (EP) .................................. 06000430

(51) Int. Cl.
*A61M 36/04* (2006.01)
(52) U.S. Cl. .......................................................... 600/3
(58) Field of Classification Search .................. 600/1–8; 604/27–45, 528; *A61N 5/00, 5/02, 36/00, A61N 36/04, 36/10, 36/12*
See application file for complete search history.

(56) References Cited

U.S. PATENT DOCUMENTS

| 4,763,642 A | 8/1988 | Horowitz |
| 4,815,449 A | 3/1989 | Horowitz |
| 4,950,232 A * | 8/1990 | Ruzicka et al. ................ 604/43 |
| 5,478,355 A * | 12/1995 | Muth et al. .................... 606/230 |
| 5,913,813 A | 6/1999 | Williams et al. |
| 5,916,143 A * | 6/1999 | Apple et al. ...................... 600/3 |
| 6,022,308 A | 2/2000 | Williams |
| 6,083,148 A | 7/2000 | Williams |
| 6,371,904 B1 * | 4/2002 | Sirimanne et al. ................ 600/3 |
| 6,398,709 B1 * | 6/2002 | Ehr et al. .......................... 600/3 |
| 6,413,204 B1 | 7/2002 | Winkler |
| 6,602,241 B2 * | 8/2003 | Makower et al. ............. 604/509 |
| 6,673,006 B2 | 1/2004 | Winkler |
| 6,786,858 B2 * | 9/2004 | Terwilliger et al. ............. 600/3 |
| 2004/0109823 A1 * | 6/2004 | Kaplan ....................... 424/1.11 |
| 2006/0293581 A1 * | 12/2006 | Plewes et al. ................. 600/407 |

FOREIGN PATENT DOCUMENTS

| DE | 198 08 170 A1 | 9/1998 |
| EP | 1 402 922 B1 | 3/2004 |
| EP | 1 568 397 A1 | 8/2005 |
| EP | 1 616 597 A1 | 1/2006 |
| WO | WO 99/40962 A1 | 8/1999 |

OTHER PUBLICATIONS

PCT/ISA/210 for PCT/EP2007/000077 dated Jun. 12, 2007.

* cited by examiner

*Primary Examiner* — Charles A Marmor, II
*Assistant Examiner* — Catherine E Burk
(74) *Attorney, Agent, or Firm* — Buchanan Ingersoll & Rooney PC (57) ABSTRACT

The invention relates to an implant for treating a cavity that is created as a result of a resection, the implant being modular and the modules being interconnectable.

27 Claims, 14 Drawing Sheets

IMPLANT FOR TREATING THE INTERNAL WALLS OF A RESECTION CAVITY

The invention relates to an implant for treating the internal walls of a cavity resulting from a resection.

The treatment of tissue in a cavity resulting from surgical removal of a tumor has become increasingly important in the past years. The subject matter of this invention is a device for radiation therapy.

EP 1402922 A1 discloses an implant of this kind. Said implant involves an inflatable chamber with devices for introduction of a radiation source.

U.S. Pat. No. 4,815,449 discloses a device of the kind in question, the implant being made of biodegradable material.

Document U.S. Pat. No. 6,673,006 discloses a device for the application of radiation therapy, in particular a radiation therapy as close as possible to the medium to be irradiated (brachytherapy).

Other known prior art documents include U.S. Pat. Nos. 6,413,204, 6,083,148, 6,022,308, 4,763,642 and 5,913,813.

Some of these devices disclosed in the prior art have dimensions that are too small, for example being for intravascular applications. Other designs comprise a balloon of cylindrical shape, where the catheter guiding the radiation source extends in the direction of the central axis.

It is an object of the invention to propose an implant that can be used in many fields of application of radiation therapy. Furthermore, the implant, which is introduced into a resection space, is intended to be elastic both in the longitudinal direction and also in the radial direction, in such a way that the implant, after deformation, is able to recover the original shape again.

In addition, the implant is intended to afford the possibility of arranging the radiation source at a variable distance from the site to be treated, i.e. to allow the radiation dose to be selected by changing the distance from the internal wall of the resection cavity.

Another object of the invention is to allow some areas, in particular the outer dimensions, to be detected by X-ray.

The invention proposes a novel device for positioning of a radiation source for treating the internal walls of a resection cavity. For example, this device can be used on resection cavities in the breast, prostate or brain, or on other resection cavities in the human body that are to be treated and that have been created by removal of a tumor.

The implant is intended to have such a degree of elastic flexibility that it can adapt to the particular geometry of the resection space.

According to the invention, this object is achieved by the fact that the implant is constructed in the form of module pairs or modules, the chain formed by these having such an elastic flexibility that it is adapted to the movements of the organ into which the chain-like implant is fitted, and that it has a guide catheter provided with a stopper, the guide catheter being able to be introduced and withdrawn through a passage arranged in the module pairs or modules.

The modular structure of the implant permits a desired optimal reversible deformability. The modules, and also a system made up of several modules, are elastic. Depending on the application, the dimension of the implant in the longitudinal direction can be modified and adapted to the application.

The module pairs are preferably designed with a spherical cap shape and can be interconnected. Likewise, the module can be designed in one piece and in the shape of a disk with outwardly facing convexities. The generally two module parts of a module pair can either be interconnected by being plugged together or are arranged loosely in a row on a guide catheter. The same applies for modules designed in one piece.

According to a particularly preferred embodiment, the connection is established by plug-in connectors arranged on the module parts. Likewise, the connection can be established by separate plug-in connectors. At the connection sites of the module parts or of the module pairs, the connections are movable in such a way that the implant made up of several module pairs can move flexibly. The implant has elastic flexibility, i.e. the deformed implant can revert to its original shape.

This elasticity can be obtained by structural elements and/or suitable materials.

The flexibility of the structure is obtained by using resilient elements that can be of various shapes, for example C-shaped, S-shaped, Z-shaped or helical. The respective shapes have different elastic constants. The shape suitable for the particular application is used.

The material elasticity is achieved by suitable choice of a biodegradable material, depending on the desired elasticity.

A list of materials is given below by way of example. This list is not to be seen as exhaustive. All related and similar substances having the required properties can be used:

Synthetic polymers, polylactic acid, in general: glycolic-acid-based and lactic-acid-based polymers and copolymers, polycaprolactones, in general polyhydroxy alkanes (PHAs), polyhydroxyalkanoic acids=all polyesters, polyethylene glycol, polyvinyl glycol, polyorthoesters, polyanhydrides, polycarbonates, polyamides, polyimides, polyimines, polyimino carbonates, polyethylene imines, polydioxanes, polyethylene oxides, polyphosphazenes, polysulfones, polyacrylic acids, polymethylmethacrylates (PMMA), polyacrylamides, polyacrylonitriles, polycyano acrylates, poly HEMA, polyurethanes, polyolefins, polystyrenes, polyterephthalates, polyfluorides, polyethylenes, polypropylenes, polyether ketones, polyvinyl chlorides, silicones, polysilicates (bioactive glass), siloxanes (polydimethyl siloxanes), hydroxyapatites, natural polymer derivatives, e.g. polyamino acids (natural and non-natural), possible with other connecting blocks such as fatty dicarboxylic acids and diols, polyester, poly-beta-amino ester, in general: polypeptides, such as albumins, alginates, cellulose, cellulosic biocomposites, cellulose acetates, chitin, chitosan, collagens, fibrins, fibrinogens, gelatins, lignins, starch composites with medium or high amounts of starch, foamed starch, soy-based plastics, neutral polysaccharides (gellan, gum, pullulan, laminarin and curdlan), protein-based polymers, such as polylysine, polyglutamates, polymalonates, polyhyaluronic acids, polynucleic acids, polysaccharides, polyhydroxyalkanes, polyisoprenes, starch-based polymers and all copolymers, such as linear, weakly branched and strongly branched, the associated dendrites, crosslinked, with functional properties (suitable surface, functional groups, hydrophilic or hydrophobic).

The plug-in connectors can also be designed as sleeve-type connectors. It is also advantageous that the plug-in connectors are secured against torsion.

According to a particularly preferred embodiment, the module parts or modules have passages for the catheters and/or guides for the radiation sources. The passages can be connected to one another and/or connected to the circumference of the module parts by means of resilient elements. This gives the desired selectable elastic flexibility in the radial direction. It is also possible for the central passages to have no plug-in connectors. It suffices, for example, if the individual elements are arranged in a row on a guide catheter. The walls of the resection cavity hold the individual elements together in their desired shape.

The implants are preferably made up of at least one module pair, said module pairs forming a flexible chain. The implant can be given any desired length by increasing the number of interconnected or unconnected module pairs. By means of the passages mounted with radial flexibility in the module parts, the catheters and the guides for the radiation sources can be easily guided through a chain-like implant. The catheters or the guides for the radiation sources can be withdrawn from the implant after treatment, with the implant remaining in the resection space.

To be able to introduce the implant into the body, it is provided with a guide catheter which has a needle at one end and a stopper at the other end. The needle can preferably be removed after insertion of the implant into the body. The stopper is deformable, such that the guide catheter, after overcoming the stop function, can be removed without any problem and in its entirety. Moreover, several pull-in catheters can be drawn simultaneously into the implant through the passages provided for them in the modules, for example in order to increase the radiation dose.

In some applications it is necessary for the implant to be detectable by X-ray, for example in the context of a standard CT treatment. Provision is therefore made to add radiologically detectable indicators to the material of the implant. For example, the radiologically detectable and biodegradable indicators are composed of Mg, Ba, Y, Zr, Sr, Sc, Ti, Nb, Fe, Ag, Yb, Nd, Gd or Ca alloys and/or compounds.

It is likewise possible, according to the invention, to make the guide catheter visible by X-ray, for example by impregnating it with barium sulfate, with metal wires inside the catheter walls, a stiffening wire, or a guide wire made completely of metal. The stiffening wire can be made of biodegradable material, plastic, or metal wire sheathed with plastic.

A particularly preferred embodiment involves the X-ray-visible material being formed from a biodegradable substance, for example from magnesium, magnesium alloys or magnesium compounds.

The indicators are preferably arranged on the periphery of the implant in such a way that the outer contours of the implant can be detected on the X-ray monitor (CT scanner), which affords considerable advantages for dosimetry. The usual diameters of the implant are between 1 cm and 5 cm, preferably 1.5 cm, 2.5 cm and 3.5 cm.

According to a particularly preferred embodiment, part of the implant or the whole of the implant is made of a biodegradable material which is provided with a net-like lattice. The lattice is made of magnesium, a magnesium alloy or a magnesium compound for detection by X-ray (CT scanner). This embodiment also has the advantage that, because of the suitable elastic material selected, it is suitable for use in the human body.

Preferably, the implant, relevant parts of the implant and/or the guide catheter are coated with antibiotic or antiseptic material, for example silver.

An important point is that the decay time of the biodegradable material is not appreciably different than the decay time of the surgical threads used for suturing the resection space. This is intended to avoid the disadvantage of the implant being able to move freely in the resection cavity.

Illustrative embodiments are depicted in the drawing, in which.

Figure 1A:
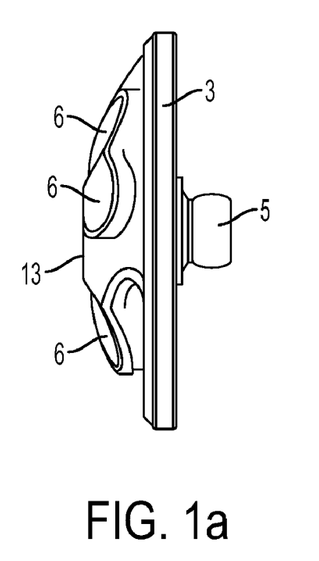
FIGS. 1a and 1b show two matching module parts.
Figure 1B:
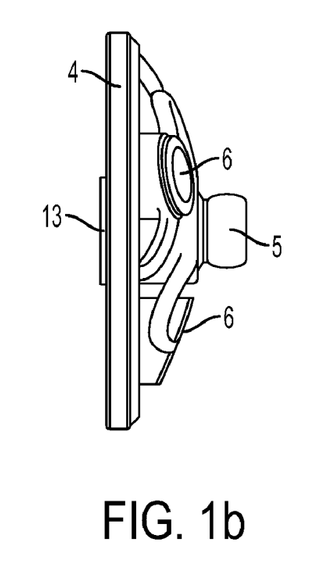
Figure 2:
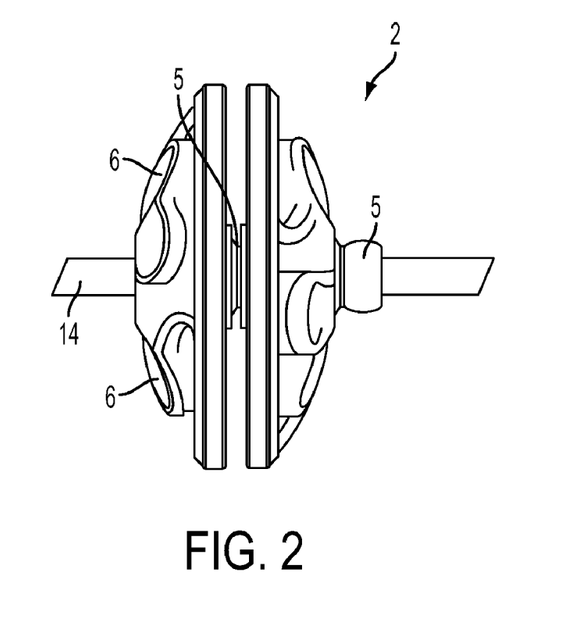
FIG. 2 shows a module pair.

Two possible module parts 3 and 4 according to the invention are shown in FIGS. 1a and 1b. The two module parts 3 and 4 have a spherical cap shape in circumference, with plug-in connectors 5 arranged in each case at the center of the module parts 3 and 4. The plug-in connectors can be mounted integrally on the module parts 3 and 4. Separate clips are likewise suitable for plugging the module parts together to form a module pair 2, as is shown in FIG. 2. The module pair 2 forms the smallest possible embodiment of an implant 1 according to the invention. In the module parts 3 and 4, passages 6 are arranged for catheters or guide elements for radiological sources for treatment of the diseased areas in the resection cavity. The catheter 14, guided through the center 13 for example, can be withdrawn after treatment, in which case it detaches from the module pairs (2, 9, 10, 11).

Figure 3:
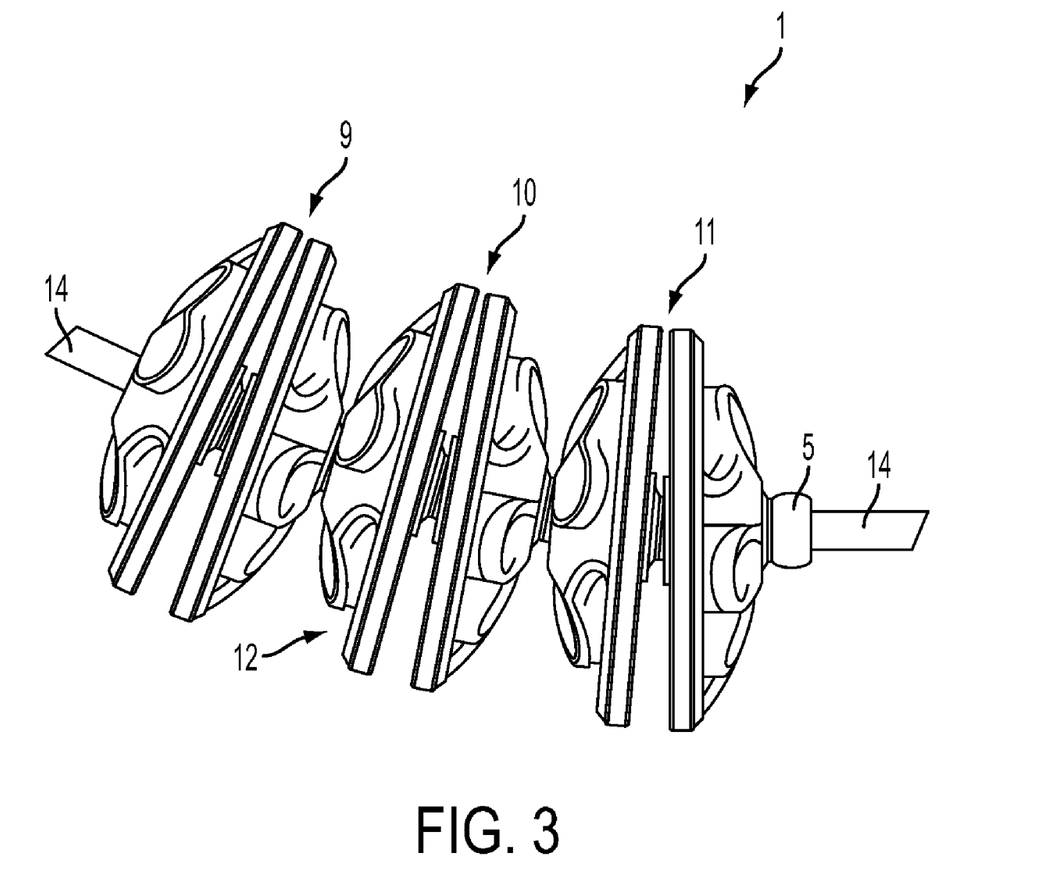
FIG. 3 shows a chain-like implant.
Figure 4:
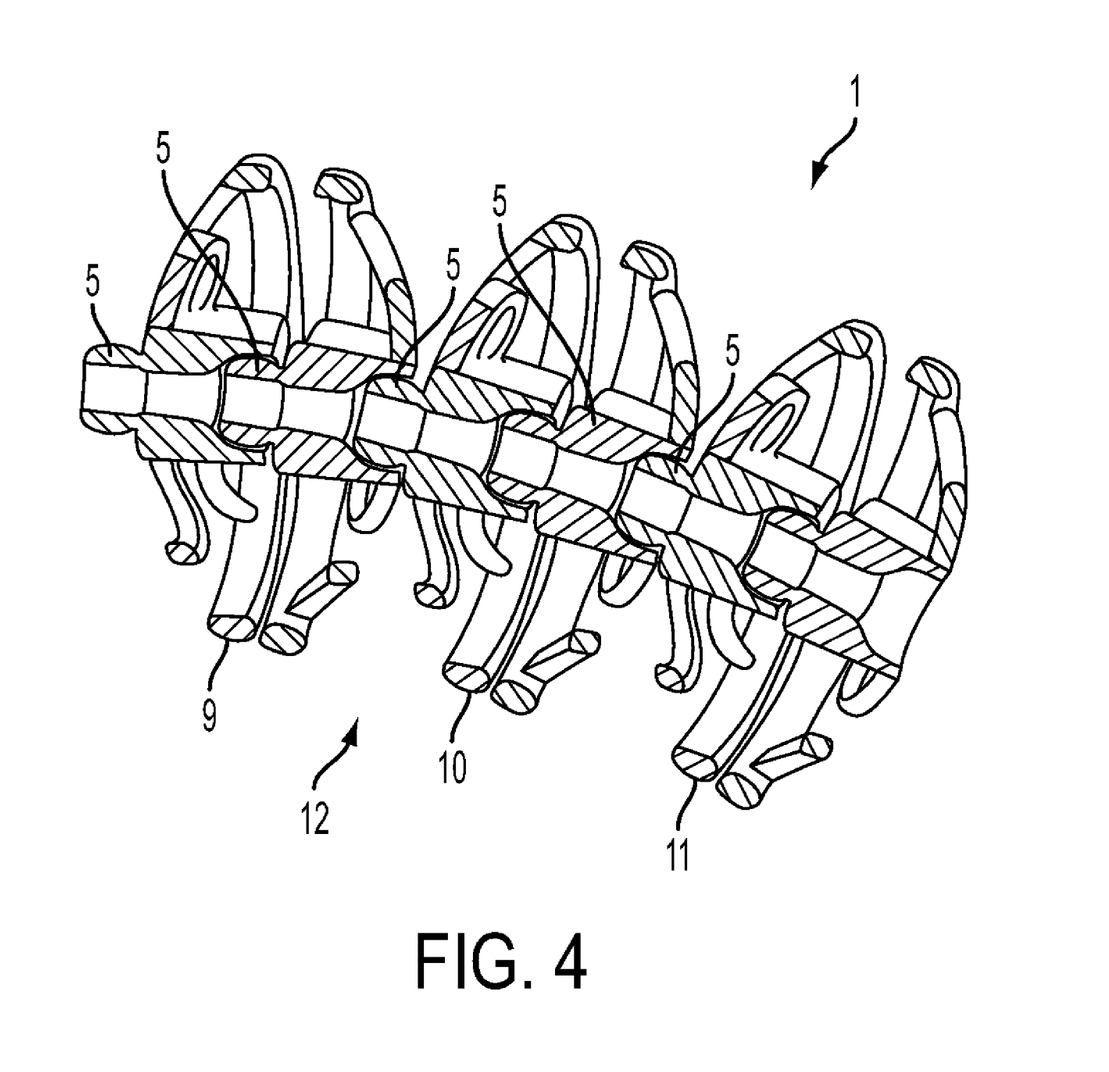
FIG. 4 shows a cross section of a chain-like implant.

FIG. 3 shows an implant 1 made up of three module pairs (9, 10, 11) and forming a chain 12. The module pairs (9, 10, 11) or chain 12 are made of biodegradable material and remain in the cavity after treatment. To permit radiological detection, substances that are visible by X-ray are added to the material. In FIG. 4, the implant can be seen from the inside.

Figure 5:
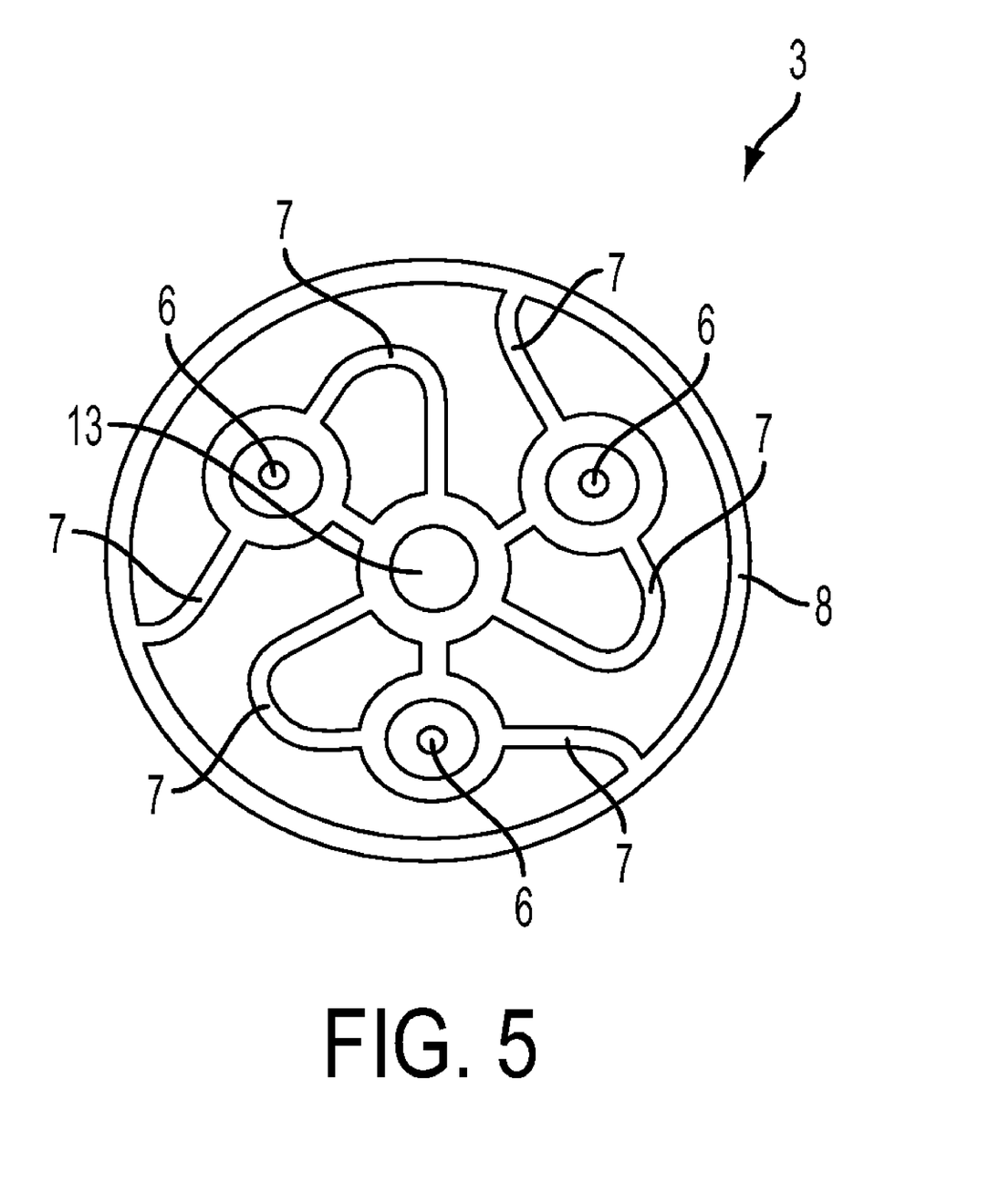
FIG. 5 shows a plan view of a module part.
Figure 6:
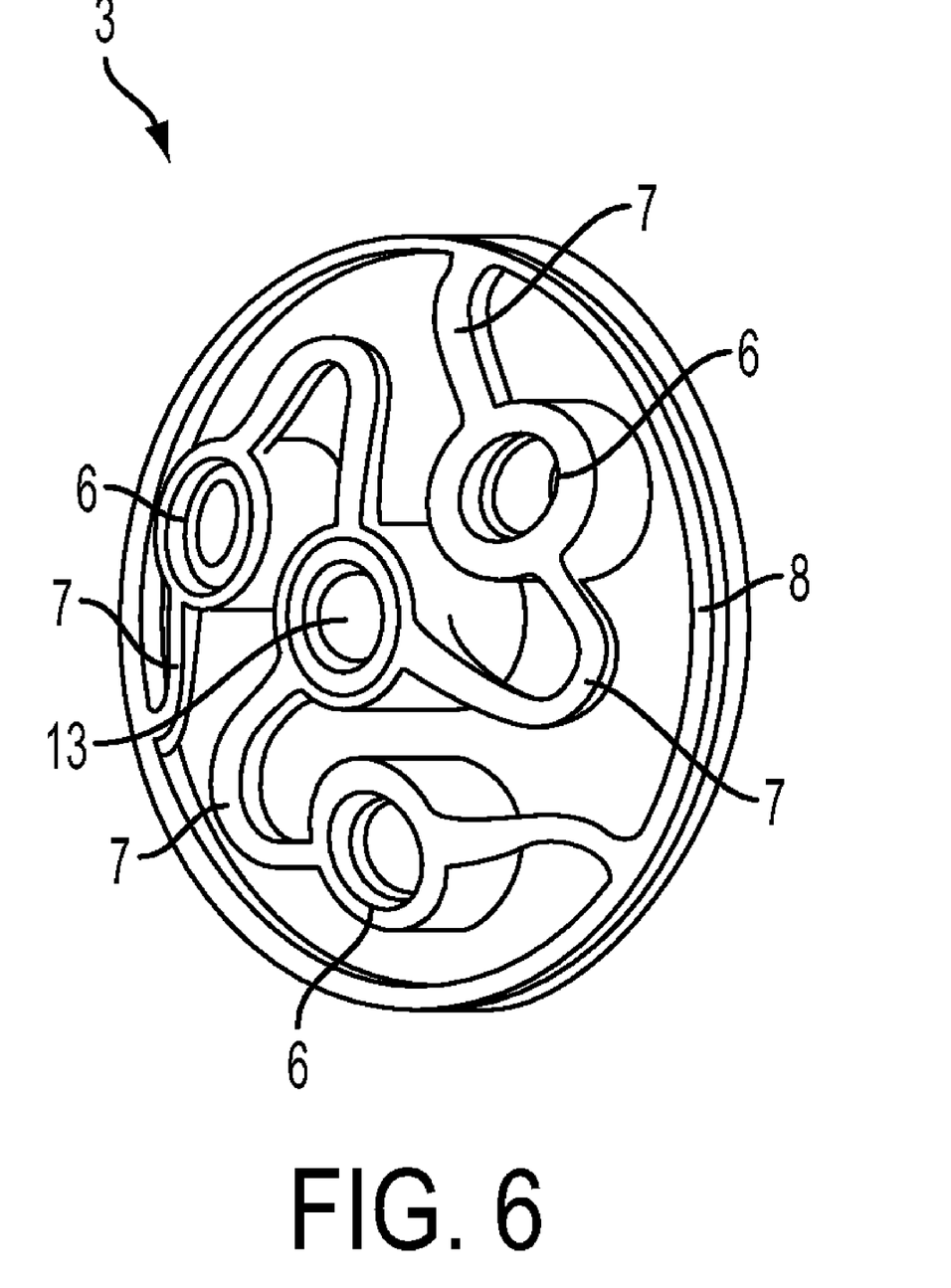
FIG. 6 shows a three-dimensional view of a module part.

FIGS. 5 and 6 show the internal structure of a module part 3. Within the circumference 8 of the module part 3 there are, in this example, four passages 6 for catheters and guide elements for treatment devices, for example radiological sources for radiation treatment. Three eccentric passages 6 are provided along with the central passage at the center 13 of the module part 3. This allows the treatment device to be placed closer to the focus of the disease. The individual passages 6 are connected elastically to one another, to the center 13 and to the circumference 8 by means of resilient elements 7 in order to ensure optimal flexibility (not too flexible and not too stiff). In this illustrative embodiment, the resilient elements 7 have an S-shaped configuration. All conceivable resilient configurations are also possible. The outer ring on the circumference 8 can be continuous or interrupted.

Figure 7:
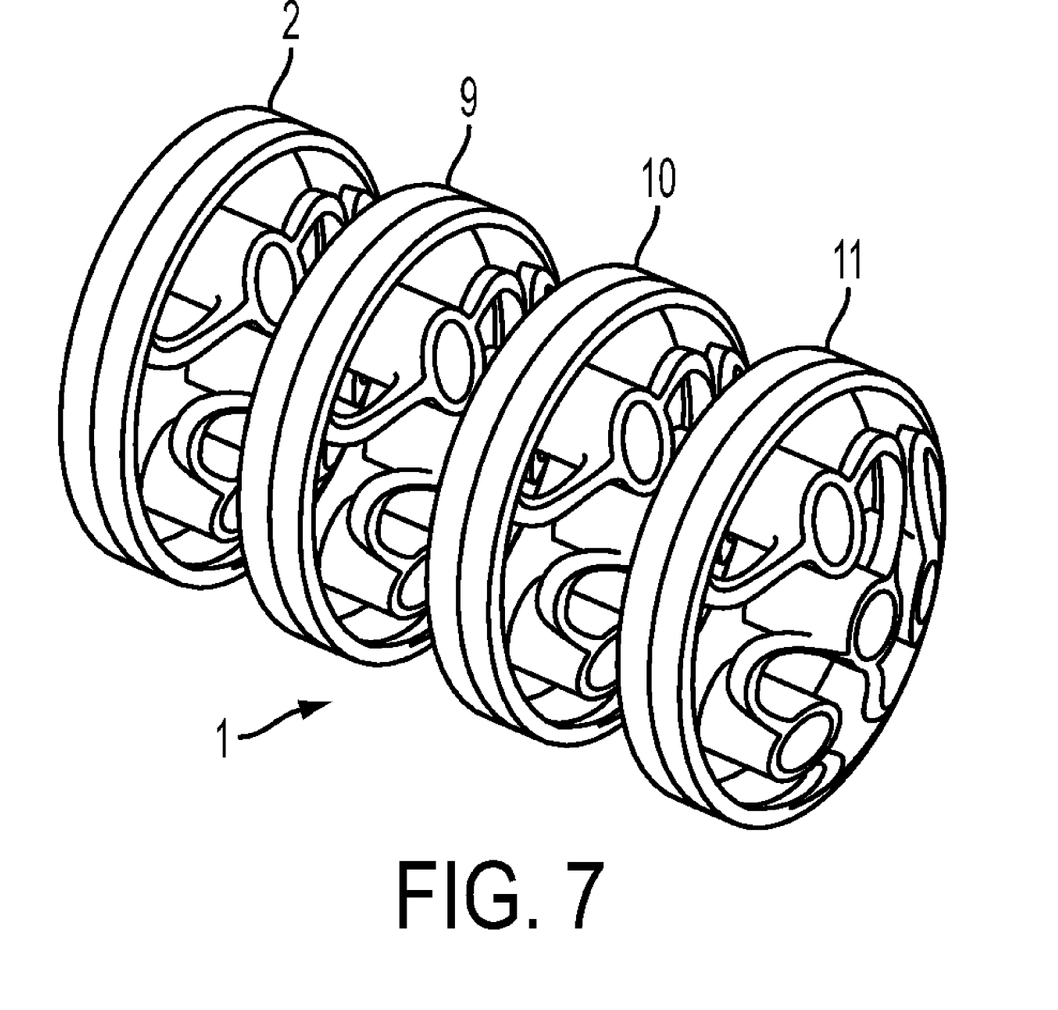
FIG. 7 shows another chain-like implant.

FIG. 7 shows a chain-like implant 1 made up of four module pairs 2, 9, 10, 11, 12. According to the invention, the number of module pairs is not limited. The chain can have as many module pairs as are needed for the application.

The advantages associated with the invention are, in particular, that the modular structure of the implant means it can be used for many applications and it has a high degree of flexibility, both in the longitudinal direction and also in the radial direction, in the module parts. Furthermore, the treatment of the walls of the resection cavity can take place sufficiently close to the area that is to be treated.

Figure 8:
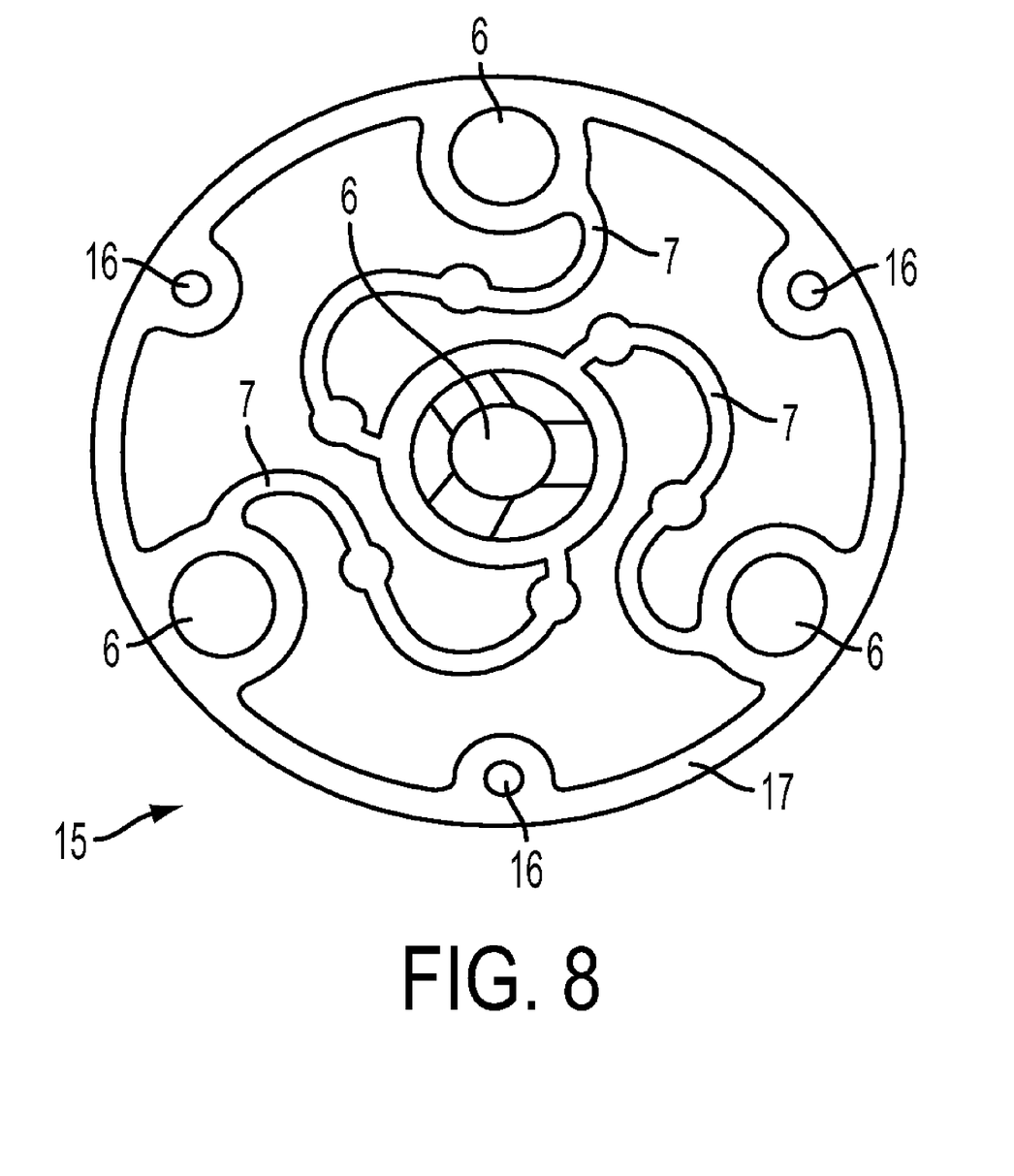
FIG. 8 shows another embodiment of a module, in a plan view.
Figure 9:
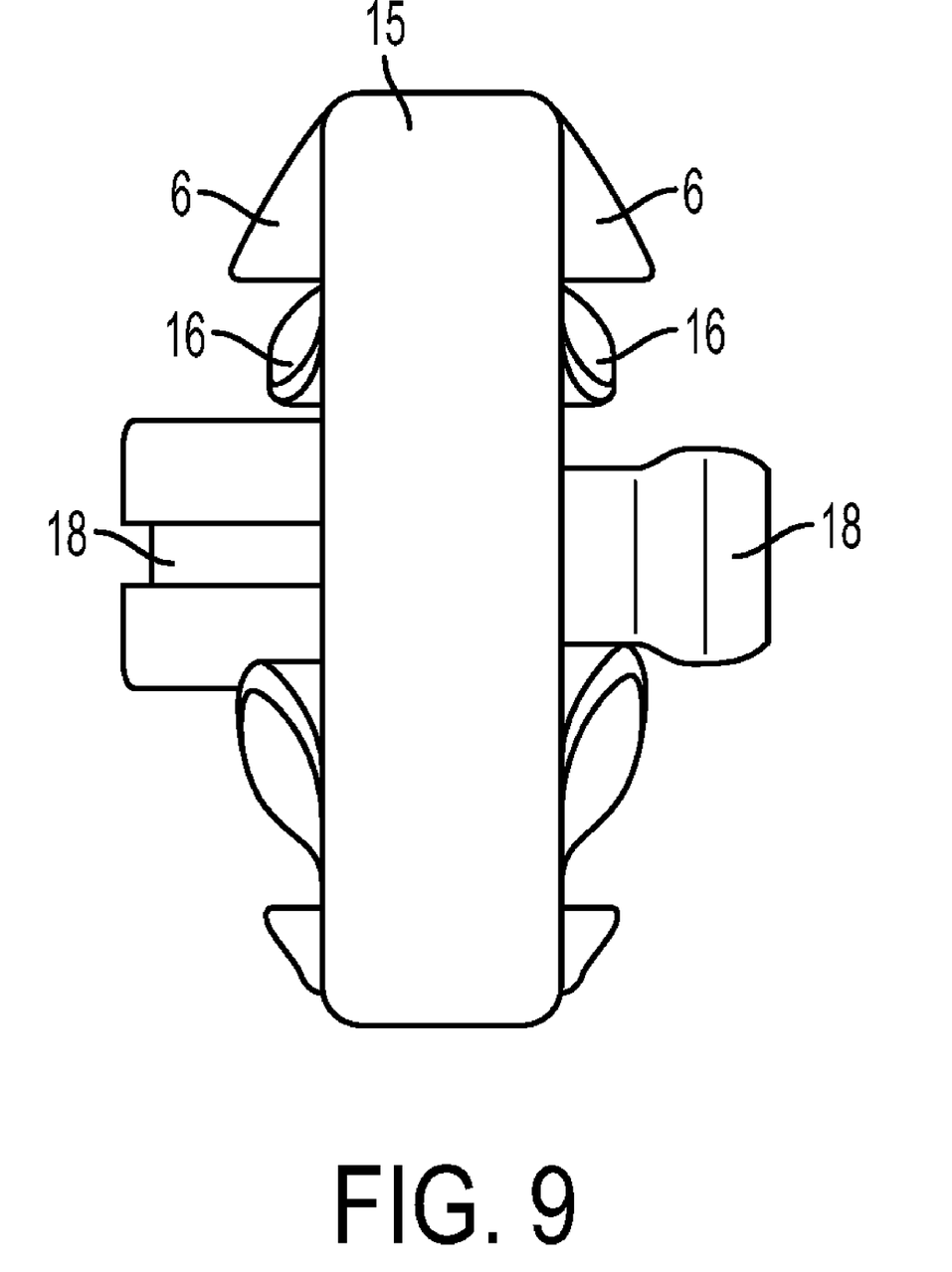
FIG. 9 shows the embodiment from FIG. 8 in a side view.
Figure 10A:
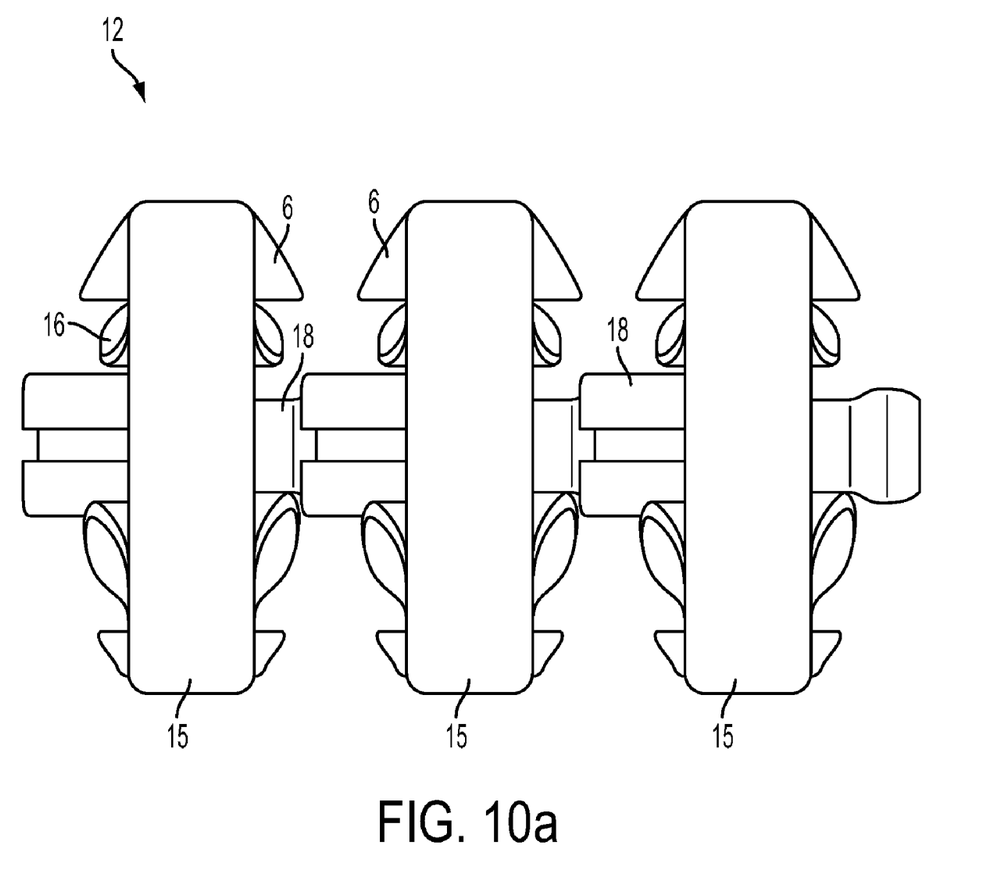
FIGS. 10a and 10b show a chain-like implant with modules in accordance with FIG. 8,
FIGS. 11a and 11b show a schematic arrangement of an implant.
Figure 10B:
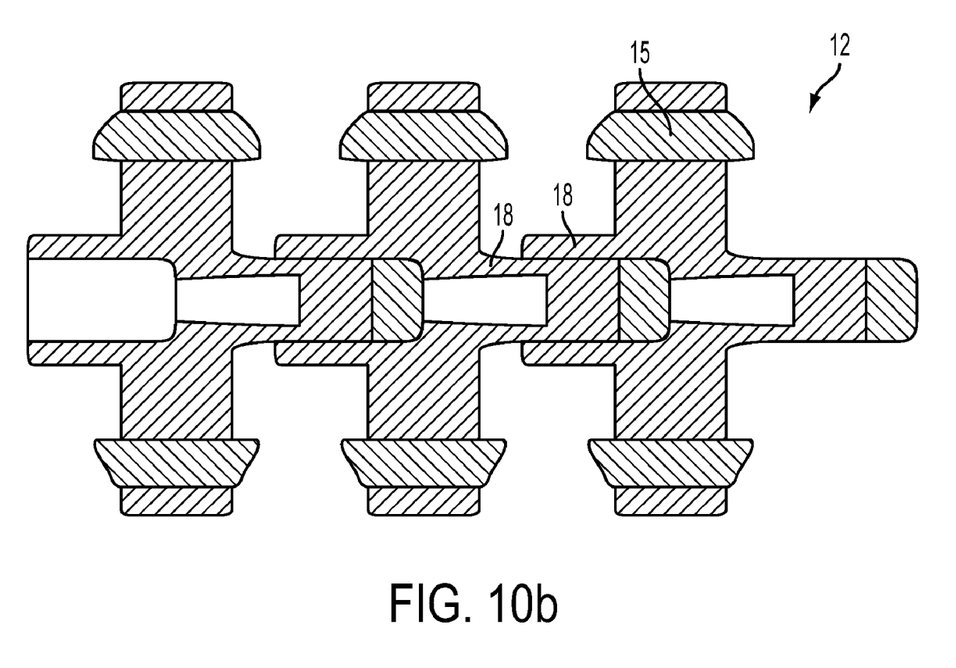

FIGS. 8 to 10 show another illustrative embodiment of an implant 1. This implant 1 is made up of at least one module 15, which is designed in one piece and, like the module pairs in the previous illustrative embodiment, has passages 6 for the catheters and radiological sources for therapy. Resilient elements 7 are also provided. The resilient elements 7 can have all conceivable shapes, for example arc-shaped, S-shaped, zigzag-shaped, C-shaped, or as small springs, etc. These elements, resilient in the radial direction, can be made of flexible plastic, for example polymers. An important aspect of the resilient elements 7 is the elastic mounting of the central passage 6 for the guide catheter. In the interior of the module 15, on the circumference of the outer ring 17 of the module 15, small passages 16 are formed that serve for introducing a radiologically detectable substance. For example, the substance can be composed of magnesium alloys. The side view in FIG. 9 shows the module 15 with the passages 6. The passages 6 are shaped in such a way that the envelope of the module sides forms circle sections on both sides. Plug-in connectors 18 are mounted integrally on both sides of the modules 15. The plug-in connectors are designed in such a way that the individual modules can be interconnected to form a chain, as is shown in FIGS. 10a and 10b. FIG. 10a shows the chain 12 closed in linear form, while FIG. 10b shows it opened in cross section.

Figure 11A:
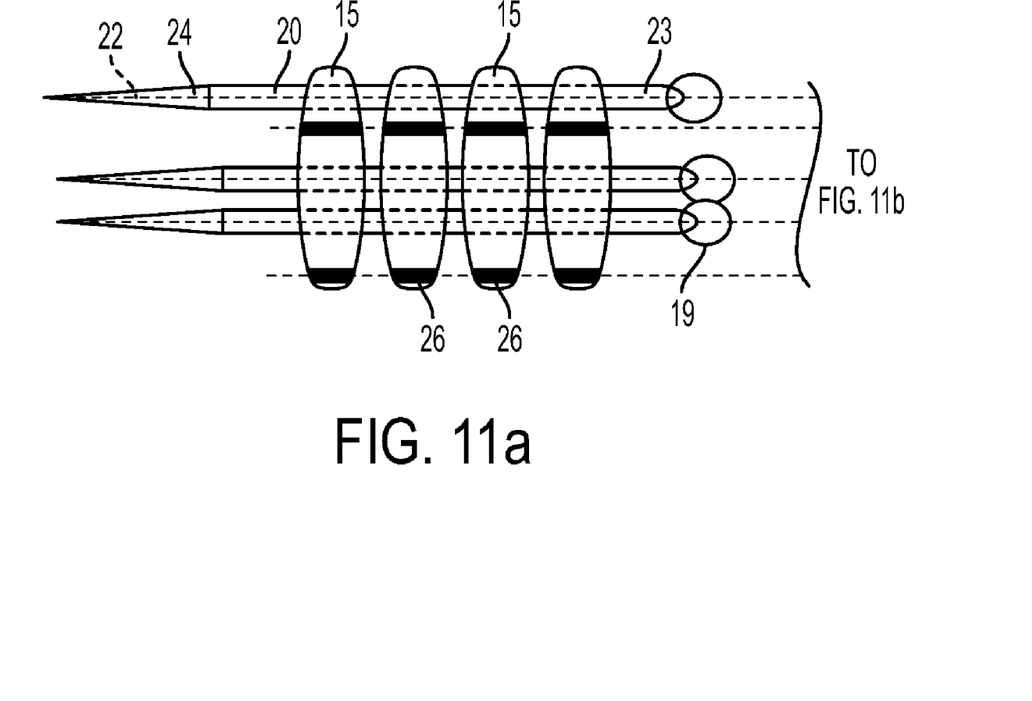
Figure 11B:
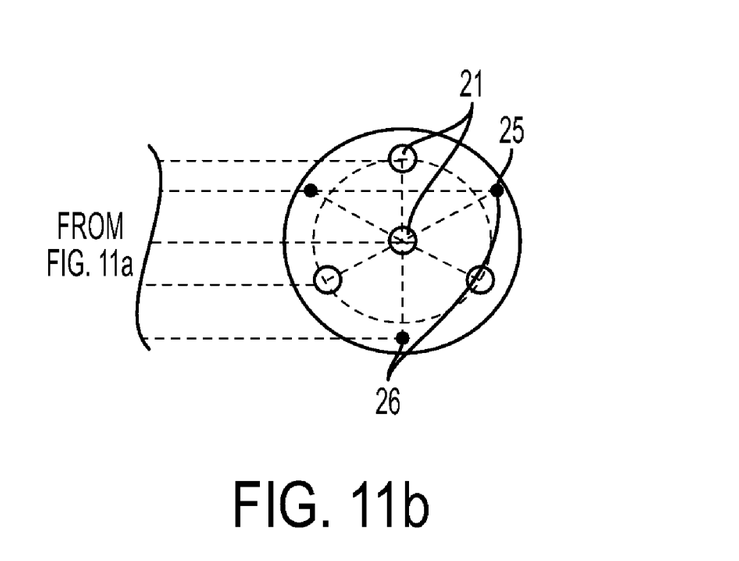

An implant system 1 according to the invention is shown in FIGS. 11a (side view) and 11b (cross section). In FIG. 11a, there are four modules 15 with three guide catheters 20 guided through the passages 21. The guide catheters 20 have needles 24 at the distal end 22 and stoppers 19 at the proximal end 23. The guide catheters 20 are made of biodegradable and antiseptic material.

Magnesium pins 26, for example, can be arranged in the openings 25 in order to allow the implant to be viewed on a CT monitor. The modules 15 are connected in a manner secure against torsion by plug-in connectors 5 (as described above). The implant 1 remains positioned in the resected cavity in such a way that a relative movement between system and body is avoided. The guide catheter 20 is closed at one end. The stopper 19 arranged at the proximal end fixes the guide catheter 20 after implantation and avoids relative movements. The guide catheter 20 can be removed from the body by traction (for example F>6 Newtons), the stopper 19 being suitably deformable (see FIGS. 14a and 14b).

Figure 12:
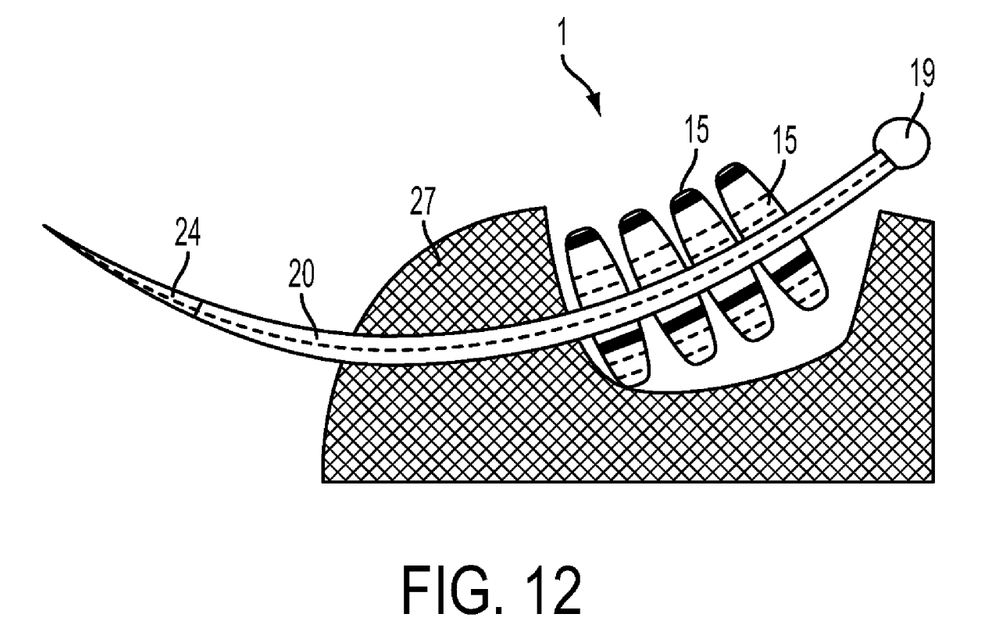
FIG. 12 shows an implant with guide catheter in the body.

FIG. 12 shows the insertion of the implant 1 into the body. The guide catheter 20 is displaceable axially with respect to the modules 15 as far as the stopper 19. The needle 24 serves to penetrate the tissue 27. It is detached from the guide catheter 20 after implantation.

Figure 13:
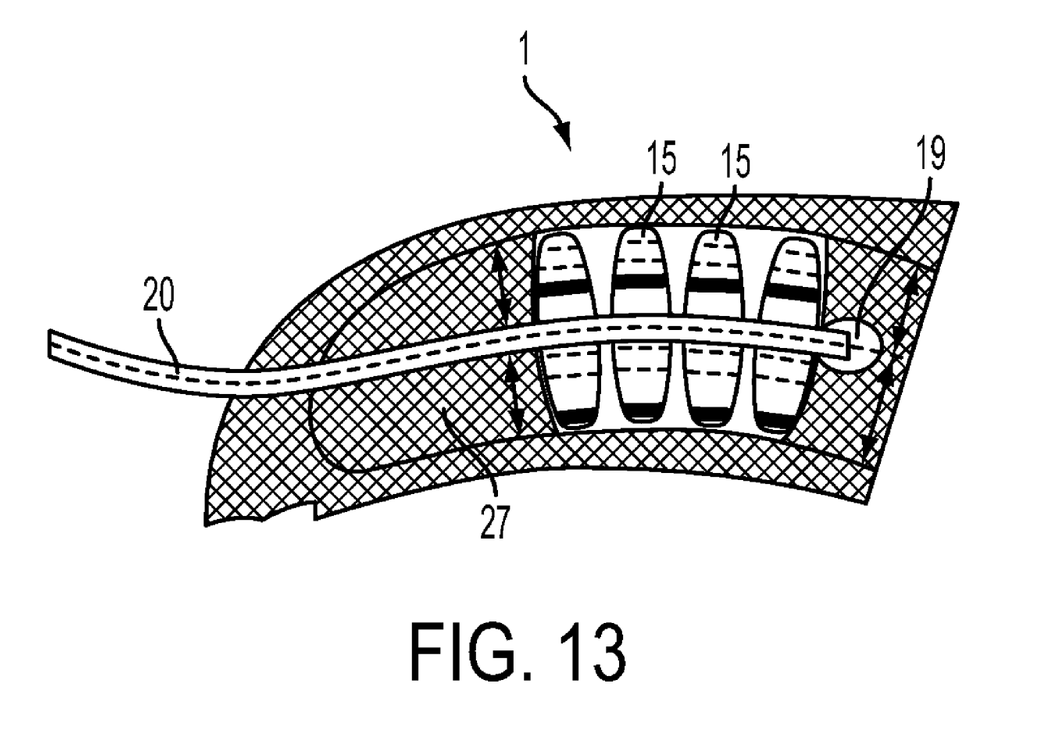
FIG. 13 shows the implant with guide catheter and stopper.

FIG. 13 shows the system 1 implanted in the body. The implant 1 is fixed at its center of gravity relative to the area to be treated. The implant 1 moves along with movements of the body part. The stopper 19 at the closed, proximal end 23 fixes the guide catheter 20. When the shape of the body part of constant volume changes as a result of movements, the body part is able to move relative to the guide catheter 20, without the guide catheter 20 being deformed.

Figure 14A:
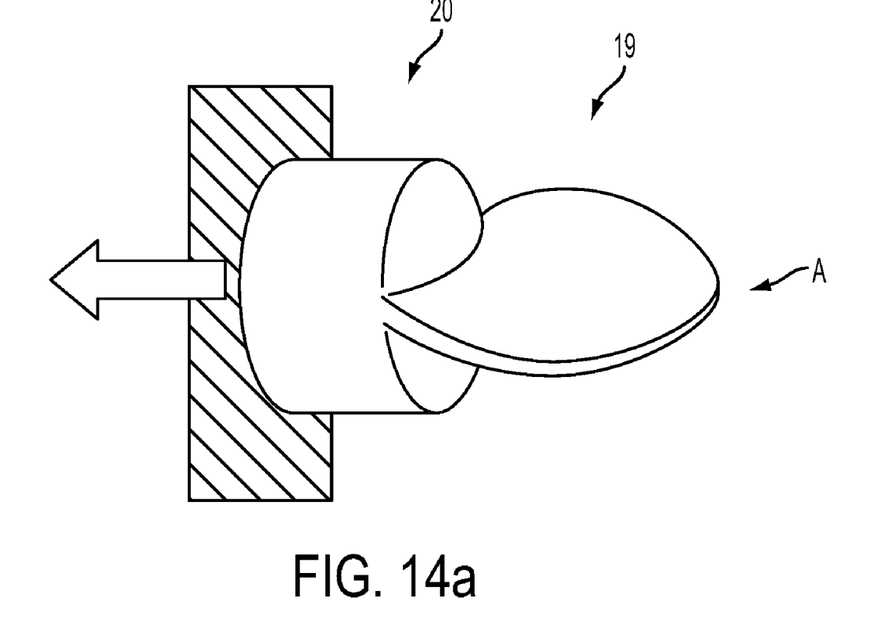
FIGS. 14a and 14b show the stopper on the guide catheter.
Figure 14B:
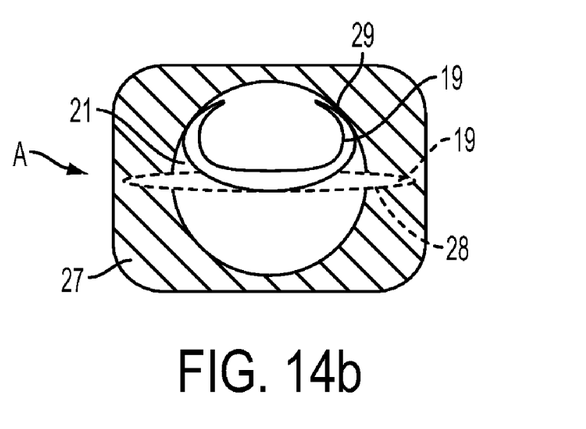

FIGS. 14a and 14b show the stopper 19 and its function. The stopper 19 of the guide catheter 20 is plastically deformable by traction. The pulling force needed for this is of the order of 3 to 10 Newtons. The plastic deformation caused by the pulling force adapts to the free surface area of the passage 21, as can be seen in FIG. 14b. The broken line 28 shows the stopper 19 in its stop function, while the solid line 29 shows the deformed stopper 19 as it is guided through the passage 21. The plastic deformation avoids brittle fracturing and undesired particle residues in the body.

LIST OF REFERENCE NUMBERS

1 implant
2 module pair
3 module part
4 module part
5 plug-in connector
6 passage
7 resilient elements
8 circumference
9 module pair
10 module pair
11 module pair
12 chain
13 center
14 catheter
15 module
16 passages
17 outer ring
18 plug-in connector
19 stopper
20 guide catheter
21 passage
22 distal end
23 proximal end
24 needle
25 opening
26 magnesium pins
27 tissue
28 broken line
29 solid line

The invention claimed is:

1. An implant for treating a cavity resulting from a resection, wherein, the implant comprises:
    a chain formed by modules being configured with an elastic flexibility adapted to movements of the organ into which the chain-like implant is to be fitted; and
    a guide catheter provided with a stopper, the guide catheter being configured to be introduced and withdrawn through a passage arranged in the modules,
    wherein the modules have resilient elements, said resilient elements being connected to a circumference and to the passage in the modules,
    and wherein the resilient elements are arranged as spokes between a more central passage and at least one of the circumference, and/or an outer ring, and/or an outer passage.

2. The implant as claimed in claim 1, wherein in circumference, at least one of the modules has a spherical cap shape on both sides and is configured in one piece.

3. The implant as claimed in claim 1, wherein the chain of modules includes module pairs, module parts or modules which have hollow plug-in devices with which the module parts, module pairs or modules are configured to be interconnected.

4. The implant as claimed in claim 3, wherein the chain of modules includes module pairs, module parts or modules are arranged loosely in a row on the guide catheter.

5. The implant as claimed in claim 3, wherein the guide catheter can be pulled in and out through the hollow plug-in devices.

6. The implant as claimed in claim 3, wherein the hollow plug-in devices are configured as sleeve-type plug-in connectors.

7. The implant as claimed in claim 3, wherein the hollow plug-in devices are secured against torsion.

8. The implant as claimed in claim 3, wherein the module parts or modules have passages for radiological sources and/or catheters.

9. The implant as claimed in claim 3, wherein the module pairs or modules form a flexible chain.

10. An implant for treating a cavity resulting from a resection according to claim 3, wherein the module parts, the module pairs or the modules have passages for introduction or arrangement of biodegradable indicators that are detectable by at least one of an X-ray or a CT scan.

11. The implant as claimed in claim 10, wherein the indicators for X-ray detection are arranged on a periphery of the implant in such a way that an external radius of the implant can be measured on a monitor.

12. The implant as claimed in claim 10, wherein the indicators for X-ray or CT detection are arranged on a periphery of the implant in such a way that a geometry of the implant can be detected.

13. The implant as claimed in claim 1, wherein the resilient elements are S-shaped, Z-shaped or helical or are made of elastic material, in order to obtain flexibility of the implant.

14. The implant as claimed in claim 1, wherein the guide catheter has a needle at one end and the stopper at another end.

15. The implant as claimed in claim 14, wherein the needle can be removed.

16. The implant as claimed in claim 14, wherein the stopper is deformable.

17. The implant as claimed in claim 1, wherein the implant is made of a biodegradable material.

18. The implant as claimed in claim 1, wherein the guide catheter is impregnated with an antiseptic material that is visible by X-ray.

19. The implant as claimed in claim 1, wherein a guide tube of the guide catheter has, in inner walls or in an interior of a catheter cavity, wires that are visible by X-ray.

20. The implant as claimed in claim 1, wherein the implant is made of a biodegradable material, said material being elastic.

21. The implant as claimed in claim 1, wherein material of the implant is reinforced by a net-like lattice.

22. The implant as claimed in claim 21, wherein the net-like lattice is made of biodegradable magnesium, a magnesium alloy or a magnesium compound.

23. The implant as claimed in claim 22, wherein biodegradable materials used in the implant will degrade almost exactly at a rate as a surgical thread used in a resection cavity for which the implant is configured.

24. An implant, according to claim 1, made of biodegradable material, and provided with magnesium pins for detection by CT scan.

25. The implant as claimed in claim 24, wherein the magnesium pins have a diameter of 0.5 mm to 5 mm and a length of 3 mm to 10 mm.

26. The implant as claimed in claim 24, comprising:
a magnesium lattice.

27. The implant as claimed in claim 26, wherein the magnesium is biodegradable.

\* \* \* \* \*